(12) United States Patent  (10) Patent No.: US 8,666,490 B1
Ryu  (45) Date of Patent: Mar. 4, 2014

(54) CAPTURE CONFIRMATION FOR MULTI-SITE PACING

(71) Applicant: Pacesetter, Inc., Sylmar, CA (US)

(72) Inventor: Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/714,256

(22) Filed: Dec. 13, 2012

(51) Int. Cl.
*A61N 1/00* (2006.01)

(52) U.S. Cl.
USPC ............................................. 607/28

(58) Field of Classification Search
USPC ............................................. 607/28
See application file for complete search history.

(56) References Cited

U.S. PATENT DOCUMENTS

| | | | |
|---|---|---|---|
| 6,128,535 A | 10/2000 | Maarse | |
| 6,760,622 B2 | 7/2004 | Helland et al. | |
| 6,915,164 B2 | 7/2005 | Bradley et al. | |
| 7,123,963 B2 | 10/2006 | Sawchuk et al. | |
| 7,286,876 B2 | 10/2007 | Yonce et al. | |
| 7,319,900 B2 | 1/2008 | Kim et al. | |
| 7,457,664 B2 | 11/2008 | Zhang et al. | |
| 7,509,170 B2 | 3/2009 | Zhang et al. | |
| 7,574,260 B2 | 8/2009 | Stalsberg et al. | |
| 7,706,866 B2 | 4/2010 | Zhang et al. | |
| 7,797,036 B2 | 9/2010 | Zhang et al. | |
| 7,890,159 B2 | 2/2011 | Zhang et al. | |
| 7,917,196 B2 | 3/2011 | Zhang et al. | |
| 7,979,113 B2 | 7/2011 | Dong et al. | |
| 7,979,124 B2 | 7/2011 | Meyer et al. | |
| 8,145,296 B2 | 3/2012 | Stalsberg et al. | |
| 2006/0155338 A1 | 7/2006 | Mongeon et al. | |
| 2007/0066998 A1 | 3/2007 | Hansen et al. | |
| 2007/0078489 A1 * | 4/2007 | Meyer et al. | 607/9 |
| 2009/0088827 A1 | 4/2009 | Tockman et al. | |
| 2010/0121396 A1 | 5/2010 | Gill | |
| 2010/0198283 A1 | 8/2010 | Zhang | |

FOREIGN PATENT DOCUMENTS

WO  WO/2006/039693  4/2006

\* cited by examiner

*Primary Examiner* — Robert N Wieland

(57) ABSTRACT

A medical device includes pacing circuitry configured to deliver during a cardiac cycle a first pacing pulse to a first site using a first electrode as a cathode electrode for the first pacing pulse and to deliver a second pacing pulse to a second site using a second electrode as a cathode electrode for the second pacing pulse. Sensing circuitry is configured to generate a differential signal between cardiac electrical activity sensed at the first electrode and cardiac electrical activity sensed at the second electrode. Capture circuitry discriminates between single site capture and multi-site capture based on the differential signal.

20 Claims, 10 Drawing Sheets

CAPTURE CONFIRMATION FOR MULTI-SITE PACING

TECHNICAL FIELD

This application relates generally to techniques for detecting capture for multi-site pacing. The application also relates to components, devices, systems, and methods pertaining to such techniques.

BACKGROUND

Congestive heart failure (CHF) is a significant health problem and the prevalence of the disorder is increasing. CHF can cause cardiac output to decrease as the heart loses its ability to efficiently pump blood. In some cases of CHF, the left ventricle ceases to contract synchronously, causing pumping action of the heart to be significantly impaired. The increased size and reduced contractility of the left ventricle further exacerbate intraventricular dyssynchrony as the depolarization delays between portions of the left ventricle lengthen. The decrease in pumping ability can lead to blood accumulation throughout the body, which may damage other organ systems.

Cardiac pacing is increasingly prescribed as treatment for CHF. The evolution of pacing devices to treat CHF has progressed from dual chamber devices that pace the right atrium and right ventricle, to devices that provide bi-ventricular pacing, and most recently to devices that provide pacing at multiple sites within one heart chamber. Multi-site pacing serves to produce a more coordinated contraction within a heart chamber leading to improved pumping action.

Cardiac pacing involves delivery of electrical stimulation pulses (pacing pulses) to the heart. Pacing pulses of sufficient energy "capture" the heart tissue by initiating a propagating wavefront of depolarization at the pacing site that causes a contraction. The energy of pacing pulses delivered for pacing therapy should be set to an appropriate energy level that reliably achieves capture without unduly reducing the battery life of an implantable device.

SUMMARY

Some embodiments described herein involve a medical device including at least a first implantable electrode configured to be disposed at a first site of a heart chamber and a second implantable electrode configured to be disposed at a second site of the heart chamber. Pacing circuitry delivers a first pacing pulse to the first site using the first electrode as a cathode electrode for the first pacing pulse and delivers a second pacing pulse to the second site using the second electrode as a cathode electrode for the second pacing pulse. The first pacing pulse and the second pacing pulse are delivered during a cardiac cycle. Sensing circuitry is configured to sense a cardiac response to the pacing pulses including sensing cardiac electrical activity at the first and second electrodes, the sensing circuitry further configured to generate a differential signal between sensed cardiac electrical activity at the first electrode and sensed cardiac electrical activity at the second electrode. Capture circuitry discriminates between single site capture, comprising capture by one of the first pacing pulse or the second pacing pulse, and multi-site capture, comprising capture by both the first pacing pulse and the second pacing pulse, based on the differential signal.

In some embodiments, the capture circuitry is configured to perform a capture threshold test to determine a capture threshold of the second site. During the capture threshold test, first and second pacing pulses are delivered to the first and second sites, respectively during multiple cycles of the capture threshold test. A pacing energy of the first pacing pulses is maintained above a capture threshold for the first site. The pacing energy of the second pacing pulses is changed (e.g., stepped up or stepped down) until a change in capture status is detected. A change in capture status occurs if multi-site capture is detected for a first cardiac cycle and single site capture is detected for one or more cardiac cycles following the first cardiac cycle when the energy of the second pacing pulses is stepped down during the capture threshold test. A change in capture status occurs if single site capture is detected for a first cardiac cycle and multi-site capture is detected for one or more cardiac cycles following the first cardiac cycle if the energy of the second pacing pulses is stepped up during the capture threshold test.

Some embodiments are directed to a medical device that includes a plurality of implantable electrodes configured to be respectively coupled to a heart chamber at a plurality of sites. A pulse generator is configured to deliver a first pacing pulse using a first pacing cathode electrode and a second pacing pulse using a second pacing cathode electrode, wherein the first pacing pulse and the second pacing pulse are delivered during a cardiac cycle. Sensing circuitry is coupled to a first sensing electrode and a second sensing electrode. The sensing circuitry is configured to sense cardiac electrical activity at the first sensing electrode and at the second sensing electrode and to develop a differential signal that cancels the cardiac electrical activity sensed at the first sensing electrode from cardiac electrical activity sensed at the second sensing electrode. Capture circuitry is configured to discriminate between single site capture by one of the first or second pacing pulses and multi-site capture by both the first and second pacing pulses based on the differential signal.

According to some aspects, the first sensing electrode is the first pacing cathode electrode and the second sensing electrode is the second pacing cathode electrode. According to some aspects, the sensing electrodes are disposed on a multi-electrode lead and the first sensing electrode comprises an electrode adjacent to the first pacing cathode electrode on the multi-electrode lead.

The sensing circuitry may include a differential amplifier having first and second differential inputs wherein the first sensing electrode is electrically coupled to the first differential input and the second sensing electrode is electrically coupled to the second differential input.

The sensing circuitry may comprise subtraction circuitry configured to subtract a first signal comprising cardiac electrical activity sensed using the first sensing electrode from a second signal comprising cardiac electrical activity sensed using the second sensing electrode.

Some embodiments involve a method of determining capture status. The method includes delivering a first pacing pulse to a first site of a cardiac chamber using a first electrode as a cathode electrode for the first pacing pulse and delivering a second pacing pulse to a second site of the cardiac chamber using a second electrode as a cathode electrode for the second pacing pulse. The first and second pacing pulses are delivered during a cardiac cycle. Cardiac activity is sensed at the first electrode and at the second electrode after delivery of the first and second pacing pulses. A differential signal is generated between the cardiac activity sensed at the first electrode and the cardiac activity sensed at the second electrode following delivery of the first and second pacing pulses. The capture status of the first and second pacing pulses is determined based on the differential signal. Determination of the capture status may include discriminating between single site capture by one of the first or second pacing pulses and multi-site capture by both the first and second pacing pulses. One or both of the energy of a subsequent first pacing pulse and the energy of a subsequent second pacing pulse may be modified based on the capture status.

DETAILED DESCRIPTION

Cardiac devices and systems may be configured to deliver pacing pulses to multiple heart chambers and/or to multiple sites within a single heart chamber. Such devices may sense cardiac electrical activity in response to the delivered pacing in order to confirm that a pacing pulse captured the heart tissue.

Cardiac resynchronization therapy (CRT) involving pacing in multiple heart chambers to increase coordination of contractions has been used as therapy for congestive heart failure (CHF). For patients with dyssynchronous left ventricular (LV) failure, CRT is helpful to reduce morbidity and mortality, however, there is variability in patent response to CRT. The variability in CRT response may be reduced by increased flexibility in selecting one or multiple sites to deliver the CRT pacing. To this goal, leads that include multiple pacing and/or sensing electrodes have been developed for placement in a single chamber, e.g., the left ventricle. Embodiments discussed herein involve approaches to determine that pacing pulses delivered to multiple sites within a single heart chamber capture the heart tissue at the multiple sites.

Figure 1:
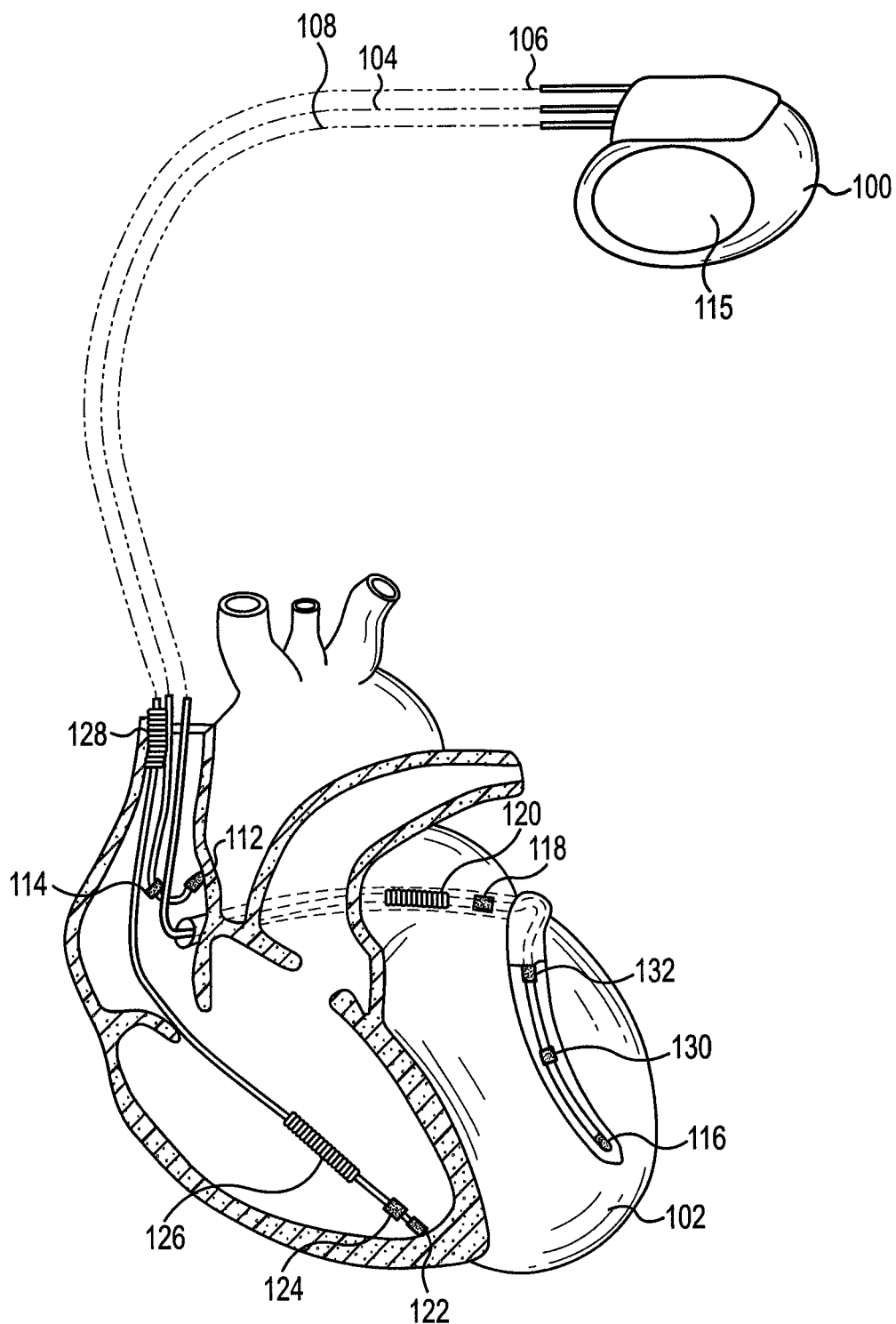
FIG. 1 is a simplified view of an exemplary implantable medical device (IMD) in electrical communication with at least three leads implanted in or on a patient's heart.

With reference to FIG. 1, a medical system includes an implantable medical device (IMD) 100 and implantable leads 104, 106, 108 suitable for sensing cardiac activity and delivering multi-chamber therapy including cardioversion, defibrillation and pacing stimulation. The IMD 100 may be a cardiac pacemaker, an implantable cardioverter defibrillator (ICD), a cardiac resynchronization therapy (CRT) pacemaker, a cardiac resynchronization therapy defibrillator (CRT-D), and the like.

The IMD 100 is configured for placement in electrical communication with the right side of a patient's heart 102 by way of a right atrial (RA) lead 104 and a right ventricular (RV) lead 106. The RA lead 104 is designed for placement in a right atrium and, in this exemplary implementation, includes an atrial tip electrode 112, which typically is implanted in the patient's right atrial appendage, and an atrial ring electrode 114. Accordingly, the RA lead 104 is capable of sensing electrical cardiac signals, and delivering stimulation in the form of pacing therapy to the right side of the heart, and in particular the right atrium.

The RV lead 106, in this exemplary implementation, includes a RV tip electrode 122, a RV ring electrode 124, a RV coil electrode 126, and a superior vena cava (SVC) coil electrode 128. Typically, the RV lead 106 is designed to be transvenously inserted into the heart 102 to place the RV tip electrode 122 in the right ventricular apex, the RV coil electrode 126 in the right ventricle, and the SVC coil electrode 128 in the superior vena cava. Accordingly, the RV lead 106 is capable of sensing electrical cardiac signals, and delivering stimulation in the form of pacing and/or shock therapy to the right side of the heart, and in particular the right ventricle.

The IMD 100 is in electrical communication with the left side of a patient's heart 102 by way of a coronary sinus (CS) 108 lead (also referred to herein as a left ventricular (LV) lead) designed for placement in the coronary sinus region. As used herein, the coronary sinus region refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The CS lead or LV lead 108, in this exemplary implementation, includes a left ventricular (LV) tip electrode 116, LV ring electrode 118, a coil electrode 120, and additional ring electrodes 130, 132 arranged proximally to the LV ring electrode 118. Typically the CS lead 108 is designed to be transvenously inserted into the heart 102 to access the coronary sinus region so as to place the LV tip electrode 116 and additional ring electrodes 130, 132 adjacent to the left ventricle, and the LV ring electrode 118 and the LA coil electrode 120 adjacent to the left atrium. Accordingly, the CS lead 108 is capable of sensing electrical cardiac signals, and delivering stimulation in the form of pacing and shock therapy to the left side of the heart.

Although three leads are shown in FIG. 1, fewer or more leads (with one or more pacing, sensing and/or shocking electrodes) may be used in order to efficiently and effectively provide pacing stimulation, cardioversion and/or defibrillation. Furthermore, any individual lead may include additional electrodes.

The IMD 100 monitors cardiac signals of the heart 102 to determine if and when to deliver stimulus pulses to one or more chambers of the heart 102. The IMD 100 may deliver pacing stimulus pulses to pace the heart 102 and maintain a desired heart rate to treat an abnormally slow heart rhythm such as bradycardia. The IMD 100 may deliver pacing stimulus pulses and/or shocking stimulus pulses to treat an abnormally fast heart rate such as tachycardia. The IMD 100 may deliver pacing stimulus pulses to multiple heart chambers and/or multi-site pacing sites within a heart chamber to treat CHF.

Cardiac pacing generally involves providing a minimum amount of energy (both voltage amplitude and pulse width) required to reliably produce capture. The term "capture" refers to the situation wherein a pacing pulse results in a propagating wavefront of depolarization that produces a contraction of the heart chamber. The term "non capture" refers to the situation wherein a pacing pulse does not initiate a propagating wavefront of depolarization that produces a contraction of the heart chamber.

The IMD 100 is capable of using various combinations of electrodes for sensing cardiac electrical activity and/or for pacing. Cardiac pacing is provided between a cathode electrode with a return path through an anode electrode. The pacing pulse delivered at the cathode electrode is generally expected to initiate the propagating depolarization wavefront, although capture at the anodal sometimes occurs. Pacing cathode electrodes may be any of the electrodes positioned in, on, or adjacent to the RA, the LA, the RV and/or the LV. Pacing anode electrodes may be electrodes positioned in, on, or adjacent to the RA, the LA, the RV and/or the LV, or other electrodes, such as an electrode disposed on the housing of the IMD 100.

Electrodes may be selected to sense cardiac electrical activity at one or more sites of one or more heart chambers. Cardiac activity can be sensed using at least two electrodes, wherein the at least two sensing electrodes can be disposed in, on or adjacent to the heart chambers or one sensing electrode can be disposed in, on or adjacent to a site of one heart chamber and another sensing electrode is disposed on the housing If the IMD. Signals generated from the sensing are sometimes referred to as cardiac electrograms (EGMs) or implantable electrograms (IEGMs).

The term "cardiac sensing and/or pacing vector" refers to the electrodes used for sensing and/or pacing with additional information about the polarity of the pacing and/or sensing. Thus, cardiac pacing and/or sensing vectors include two pieces of information including the at least two electrodes used for the pacing and/or sensing, and the polarity of the pacing and/or sensing.

Figure 2:
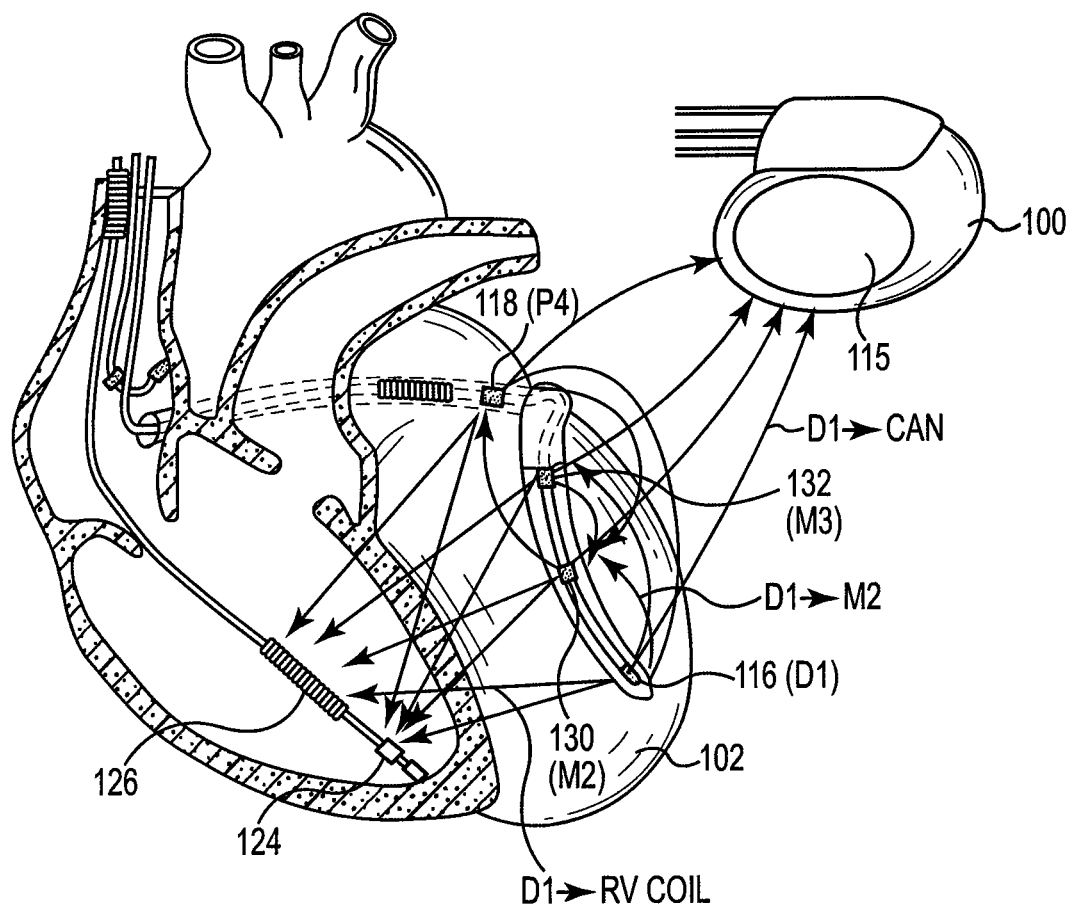
FIG. 2 illustrates exemplary cardiac vectors available using the implanted leads shown in FIG. 1.

FIG. 2 illustrates examples of some cardiac pacing and/or sensing vectors that are available using the multi-site CS lead 108. As illustrated in FIG. 2, the CS lead 108 has four LV electrodes 116, 130, 132, 118. The LV electrodes 116, 130, 132, 118 are further identified by respective positions—distal 1 (D1) 116, middle 2 (M2) 130, middle 3 (M3) 132 and proximal 4 (P4) 118. Optionally, the CS lead 108 may have any number of LV electrodes and any combination of such electrodes may be utilized to form sensing and/or pacing vectors.

In FIG. 2, the polarities of a number of pacing and/or sensing vectors are indicated by arrows. Pacing and/or sensing vectors exist between various electrodes on the left side of the heart, D1, M2, M3, P4, which are referred to as "bipolar" vectors. In general, the term "bipolar" is used herein to describe pacing or sensing between two adjacent electrodes or between two electrodes in the same heart chamber. FIG. 2 shows a number of pacing and/or sensing vectors 199 that exist between the left side electrodes, D1, M2, M3, P4 and the RV coil electrode 126 and/or the RV ring electrode 124. These vectors are sometimes referred to as "extended bipolar" vectors. In general, the term "extended bipolar vector" is used to describe a pacing or sensing vector between two electrodes in different heart chambers. In some cases, the IMD may include an electrode 115 disposed on the housing or header of the implantable device, e.g., a case or can electrode. As illustrated in FIG. 2, pacing and/or sensing vectors exist between the left side electrodes D1, M2, M3, P4 and the housing electrode 115. These pacing and/or sensing vectors are referred to herein as "unipolar" vectors, indicating pacing or sensing between an electrode disposed in or on a heart chamber and an electrode disposed on the implantable housing. For example in FIG. 2, arrow labeled D1→M2 illustrates a bipolar pacing/sensing vector between electrode D1 116 and electrode M2 130; the arrow labeled D1→RV Coil illustrates an extended bipolar pacing/sensing vector between electrode D1 116 and the RV coil electrode 126; and the arrow labeled D1→Case illustrates a unipolar pacing/sensing vector between electrode D1 116 and the housing electrode 115. In some cases, pacing and/or sensing vectors can incorporate more than two electrodes. For example, the pacing vector RV ring→SVC coil+ can is a vector from the RV ring to the SVC coil electrically connected to the case electrode. Although many more pacing and/or sensing vectors exist for the device than are indicated by arrows in FIG. 2, the pacing/sensing vectors identified in FIG. 2 illustrate the concepts of bipolar, extended bipolar, and unipolar pacing/sensing vectors. These concepts can be applied to other electrode combinations to may be used to form additional bipolar, extended bipolar and unipolar pacing and/or sensing vectors.

Figure 3:
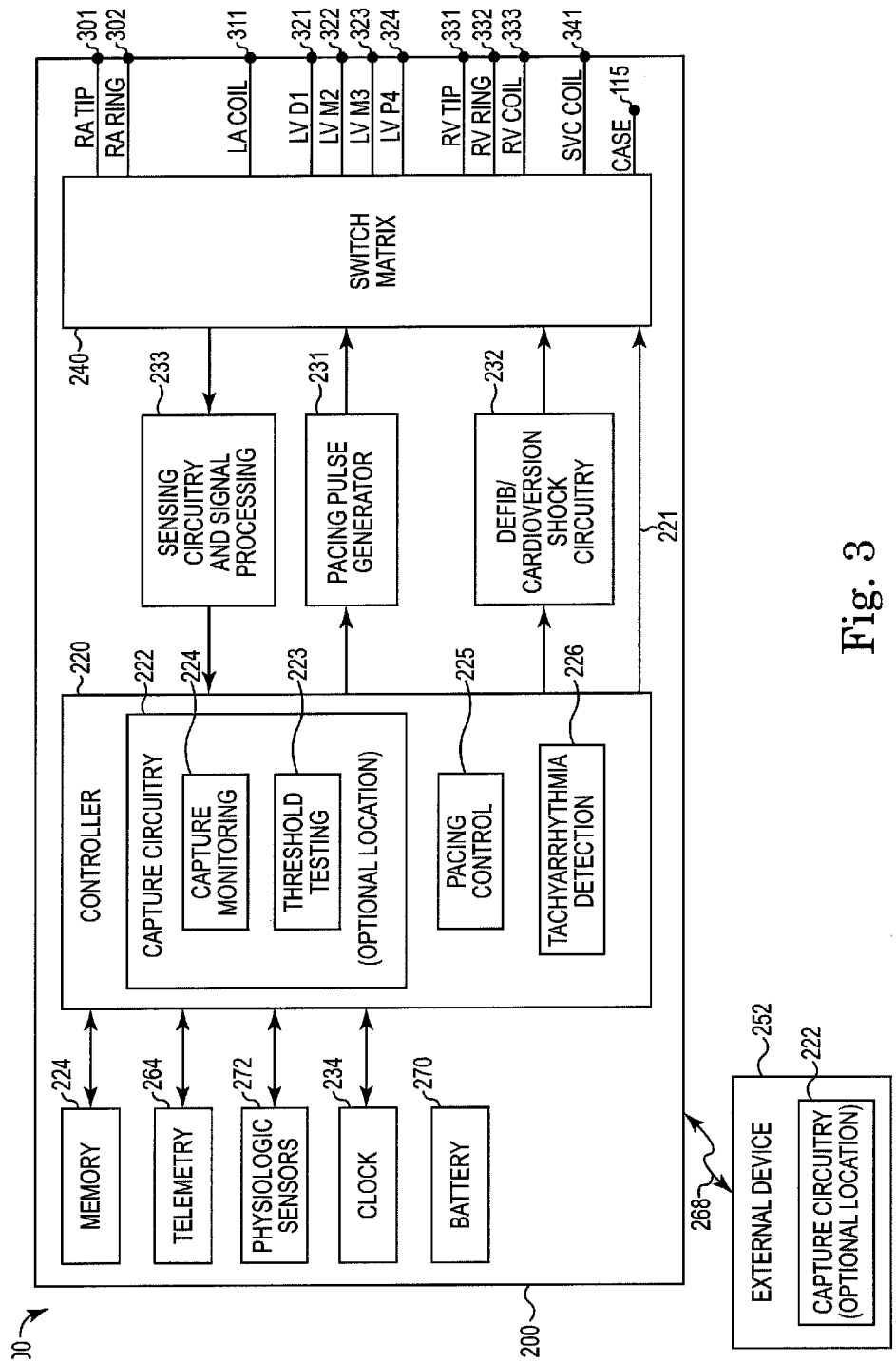
FIG. 3 is a functional block diagram of the IMD of FIG. 1.

FIG. 3 is a block diagram of exemplary internal components of the multi-chamber IMD 100 shown in FIG. 1. While a particular multi-chamber device is shown, the multi-chamber device is for illustration purposes only, and one of ordinary skill in the pertinent art could readily duplicate, eliminate or disable the appropriate circuitry in any desired combination to provide a device capable of treating the appropriate chamber(s) with cardioversion, defibrillation, and/or pacing stimulation.

The IMD 100 includes a housing 200 that includes the following terminals for the various electrodes disposed in, on, or adjacent to the heart chambers: RA tip terminal 301, RA ring terminal 302, LA coil terminal 311, LV D1 terminal 321, LV M2 terminal 322; LV M3 terminal 323, LV P4 terminal 324, RV tip terminal 331, RV ring terminal 332, RV coil terminal 333, and SVC coil terminal 342.

The input terminals 301-341 are electrically coupled to the corresponding electrodes 112-132 (shown in FIG. 1) and to switch matrix 240. The switch matrix 240 is capable of coupling any of the electrodes shown in FIG. 1 in various combinations to other components of the IMD, including the sensing circuitry, the pacing pulse generator, and the defibrillation/cardioversion shock circuitry.

The IMD 100 includes a programmable controller 220, which is configurable to control the operation of the IMD 100. The controller 220 typically includes a microprocessor, or equivalent control circuitry, and may be specifically designed for controlling the delivery of stimulation therapy and/or for sensing cardiac electrical activity and/or for performing other functions. For example, the controller 220 may include various registers to facilitate implementation of program steps, RAM and/or ROM memory, logic and/and timing circuitry, state machine circuitry, and/or I/O circuitry.

The controller 220 includes a pacing control module 225 configured to control the delivery of pacing therapy. For example, the pacing control module 225 may control the delivery of timed atrial and/or ventricular pacing pulses that treat bradyarrhythmia. In some cases, the pacing control module may control the delivery of antitachyarrhythmia pacing pulses (ATP) and/or the pacing control module may control delivery of pacing pulses delivered as part of a CRT. The controller 220 may optionally include tachyarrhythmia detection circuitry 226 configured to detect atrial and/or ventricular tachyarrhythmias. If a tachyarrhythmia is detected by the tachyarrhythmia detection circuitry 226, an appropriate therapy can be delivered to terminate the tachyarrhythmia. In some cases, the therapy can include ATP which involves high energy paces that can slow fast rhythms. For tachyarrhythmias that are more serious or are more difficult to terminate, cardioversion and/or defibrillation shocks generated by the defibrillation/cardioversion shock circuitry 232 may be delivered to the heart to reestablish a normal sinus rhythm.

The pacing pulse generator and defibrillation/cardioversion circuitry deliver pacing pulses and/or shocks via electrodes that are coupled to the pacing pulse generator 231 and/or defibrillation/cardioversion circuitry 232 through a programmable switch matrix 240. In general, any of the electrodes 112-132 and case electrode 115 can be coupled in various combinations to the pacing pulse generator 231 and/or defibrillation/cardioversion circuitry 232. The controller 220 may be capable of controlling which of the electrodes are coupled to the sensing 233, pacing 231, and defibrillation circuitry 232 via control signal 221.

The sensing/signal processing circuitry 233 can provide signal filtering, amplification, analog to digital (A/D) conversion, and or other processing or conditioning of the sensed signals to condition the sensed signals for output to the controller 220. The sensing circuitry 233 may include multiple sensing channels that capable of operating in parallel, each sensing channel configured to receive sensed signals from electrodes selectable through the switch matrix 240. The sensing/signal processing circuitry 233 may filter, amplify, convert the sensed signals to digital form and/or otherwise condition the sensed signals so that they are suitable for input to the controller 220.

The controller 220 may analyze the signals and/or may use the signals and/or results of the signal analysis to inhibit or trigger delivery of pacing pulses, initiate pacing delays, evaluate patent conditions, detect tachyarrhythmia and/or detect capture, non capture, or other cardiac response to pacing pulses delivered to the heart, among other functions. The controller 220 may store the signals, analysis, and/or information about the signals in the memory 224, and/or may wirelessly transmit the signals, analysis, and/or information about the signals to an external device 290.

The memory 224 may be a computer-readable storage medium such as a ROM, RAM, flash memory, and/or other type of memory. The controller 220 is coupled to the memory 224 by a suitable data/address bus. The memory 224 may store programmable operating instructions, parameters and thresholds used by the controller 220, as required to customize the operation of IMD 100 to suit the needs of a particular patient. For example, in reference to the approaches discussed herein, the memory 224 may store recorded capture thresholds identified through a capture threshold test, thresholds used to detect single site or multi-site capture, morphology templates for determining capture status and the like.

The IMD 100 includes a battery 270 that provides operating power to the circuits shown within the housing 200, including the controller 220. The IMD 100 may include a physiologic sensor 272 such as an accelerometer and/or respiration sensor. A signal generated by the physiologic sensor indicates the patient's exercise level and/or hemodynamic requirements and may be used to adjust a pacing rate according to exercise level and/or hemodynamic requirements. Clock circuitry 234 generates signals used to time various pacing delays, e.g., atrioventricular (AV) pacing delays, ventriculoatrial (VA) pacing delays, interventricular (IV) pacing delays and/or intersite (IS) pacing delays, among other types of possible delays. The clock may be used to measure the time between atrial and/or ventricular cardiac cycles for the purpose of determining atrial and/or ventricular heart rates and/or to measure the time between portions of a single cardiac cycle, for example. The clock 234 may be configured to measure elapsed time based on start and stop control signals from the controller 220. In some cases, the clock 234 may track the time elapsed between capture threshold searches and/or between other scheduled processes. For example, the elapsed time between capture threshold searches may be compared to a predetermined time period to determine whether to perform another capture threshold search.

Various operating parameters of the IMD 100 may be non-invasively programmed into the memory 224 through a telemetry circuit 264 in communication with an external device 252 which may comprise a device programmer and/or diagnostic system analyzer. The telemetry circuit 264 allows intra-cardiac electrograms, cardiac waveforms of interest, detection thresholds, status information relating to the operation of IMD 100, and the like, to be sent to the external device 252 through a wireless communication link 268. In some cases, the external device 252 may include capture circuitry 222 that communicates with the IMD 100 to perform capture threshold tests, e.g., multi-site capture threshold test, and/or capture verification for pacing.

Capture circuitry 222 may optionally be disposed within the IMD 100 or may be optionally disposed within the external device, as indicated in FIG. 3. For implementations wherein the capture circuitry 222 is disposed in the IMD 100, the multi-site capture detection approaches described herein may be implemented implantably with minimal or no interaction with the external device 252. The capture circuitry 222 is configured to determine whether pacing pulses delivered to various heart chambers and/or to multiple sites within the heart chambers produce capture. The capture circuitry 222 may be further configured to identify pacing responses other than capture, such as fusion of a depolarization initiated by a pacing pulse and an intrinsic depolarization. With regard to the multiple electrodes 116-132 disposed on the CS lead 108 (FIG. 1), when multiple sites are paced during a cardiac cycle, the capture circuitry can be configured to distinguish between multi-site capture and single site capture as discussed in more detail below. For example, the capture circuitry may be configured to implement one or more of the processes outlined by the flow diagrams of FIGS. 6-10. In the case of single site capture, the capture circuitry 222 may be configured to determine which of the pacing pulses was not captured. The capture circuitry may determine if none of the pacing pulses produce capture.

The capture circuitry 222 may include a capture threshold module 223 arranged to determine capture thresholds for pacing sites. To determine the capture threshold of a test site, the capture threshold module 223 performs a threshold test which causes the pacing energy (voltage amplitude and/or pulse width) delivered to the test site to be modified over a series of cardiac cycles until a change in capture status is detected. The point at which the change in capture status occurs indicates the capture threshold at the pacing site under test.

For example, in a step up capture threshold test, the pacing energy of the site being tested is initially set to be too low to produce capture. The pacing energy is increased over a series of cardiac cycles until capture is detected at the test site. The pacing energy of the pacing pulse that causes the capture status of the test site to change from non capture to capture indicates the capture threshold of the test site. In a step down capture threshold test, the energy of the pacing pulses delivered to the test site is initially high to ensure capture. The pacing energy delivered to the test site is stepped down over a series of cardiac cycles until the capture status of the test site changes from capture to non capture. The energy of the pacing pulse delivered just before loss of capture indicates the capture threshold at the test site.

The capture circuitry 222 may include a capture monitoring module 224 configured to monitor the capture status of pacing pulses delivered at times other than during a capture threshold test. For example, the capture circuitry may monitor the capture status for pacing pulses delivered as part of a prescribed patient therapy. If loss of capture is detected during the monitoring, the pacing energy for the non-captured site or sites may be increased until capture at the site is restored. In some cases, if the monitoring indicates a loss of capture, a threshold test may be performed or scheduled to re-evaluate capture thresholds for the pacing sites.

Multi-electrode leads, such as the LV lead 108 illustrated in FIGS. 1 and 2 allow for pacing multiple sites within a heart chamber. Pacing multiple sites within a heart chamber either simultaneously or in phased sequence during a cardiac cycle can cause a more coordinated contraction in the heart chamber. Embodiments described herein involve approaches to detect capture by one or more pacing pulses delivered to pacing sites within a heart chamber during a cardiac cycle.

As previously discussed, pacing pulses are applied to the heart tissue at a pacing cathode electrode with a return path through a pacing anode electrode. In most cases, capture of the heart tissue is initiated by the pacing pulse at the pacing cathode site. Pacing pulses may be applied to the heart tissue using a variety of pacing vectors comprising various pacing electrodes as discussed above. Pacing pulses applied simultaneously or in phased sequence to multiple sites in a heart chamber through multiple cathode electrodes during a cardiac cycle may capture the heart tissue at the multiple sites. In this scenario, each pacing pulse initiates a propagating depolarization wavefront from its respective site, and the multiple propagating depolarization wavefronts emanating from the multiple sites combine to cause a depolarization of the chamber.

Figure 4:
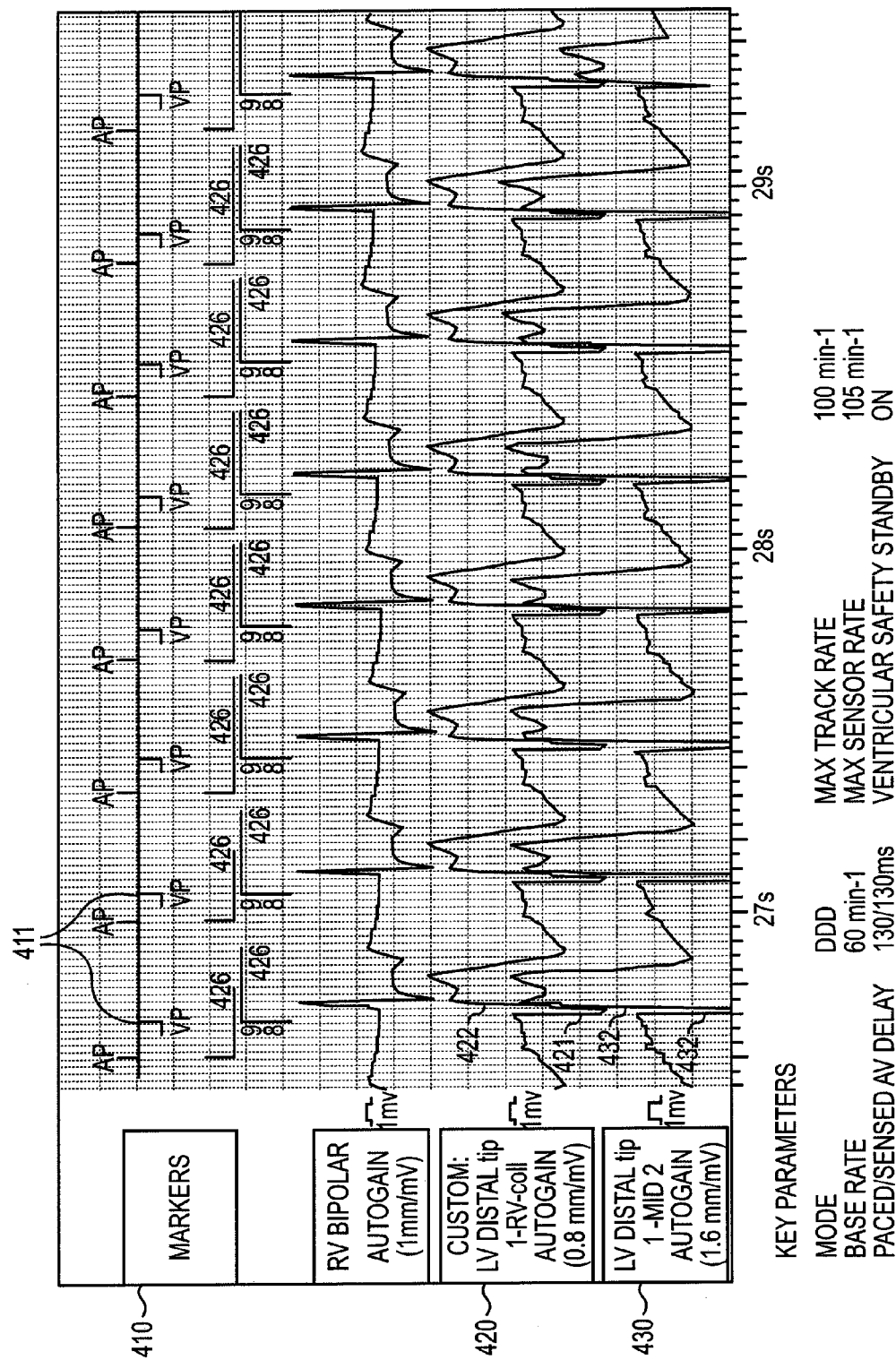
FIGS. 4, 5, and 6 show electrogram (EGM) traces illustrating multi-site capture and single site capture.

FIG. 4 illustrates EGMs sensed using various sensing vectors following capture by pacing pulses delivered to a single site of the LV lead. In this example, the LV distal tip is used as the pacing cathode electrode and the case electrode is used as the pacing anode electrode. The first trace 410 is the marker channel and indicates delivery of the ventricular paces 411 by the IMD.

Sensing cardiac activity is sensitive to the sensing configuration and to the location of the sensing. For example, a signal sensed using one or more electrodes that are in physical contact with or very close to the heart tissue will be dominated by the local cardiac electrical activity at the sensing site. In the example of FIG. 4, the cardiac electrical activity is sensed using two sensing vectors. As shown by the first LV EGM 420, the cardiac electrical activity is sensed from the LV distal tip D1 to the RV coil electrode. In addition, as shown by the second LV EGM 430, the cardiac electrical activity is sensed from the LV distal tip D1 to the LV ring electrode (M2), the M2 electrode being the closest electrode to D1 on the LV lead. The morphology of the cardiac electrical signal that follows each pacing pulse, sensed on both EGM channels 420, 430, indicates capture at the single site. In this case, the capture morphology of the cardiac activity signal is recognizable on both EGMs 420, 430 at least by the first sharp downward transition 421, 431 after delivery of the pacing pulse, followed by a significant rapid upward transition 422, 432.

Figure 5:
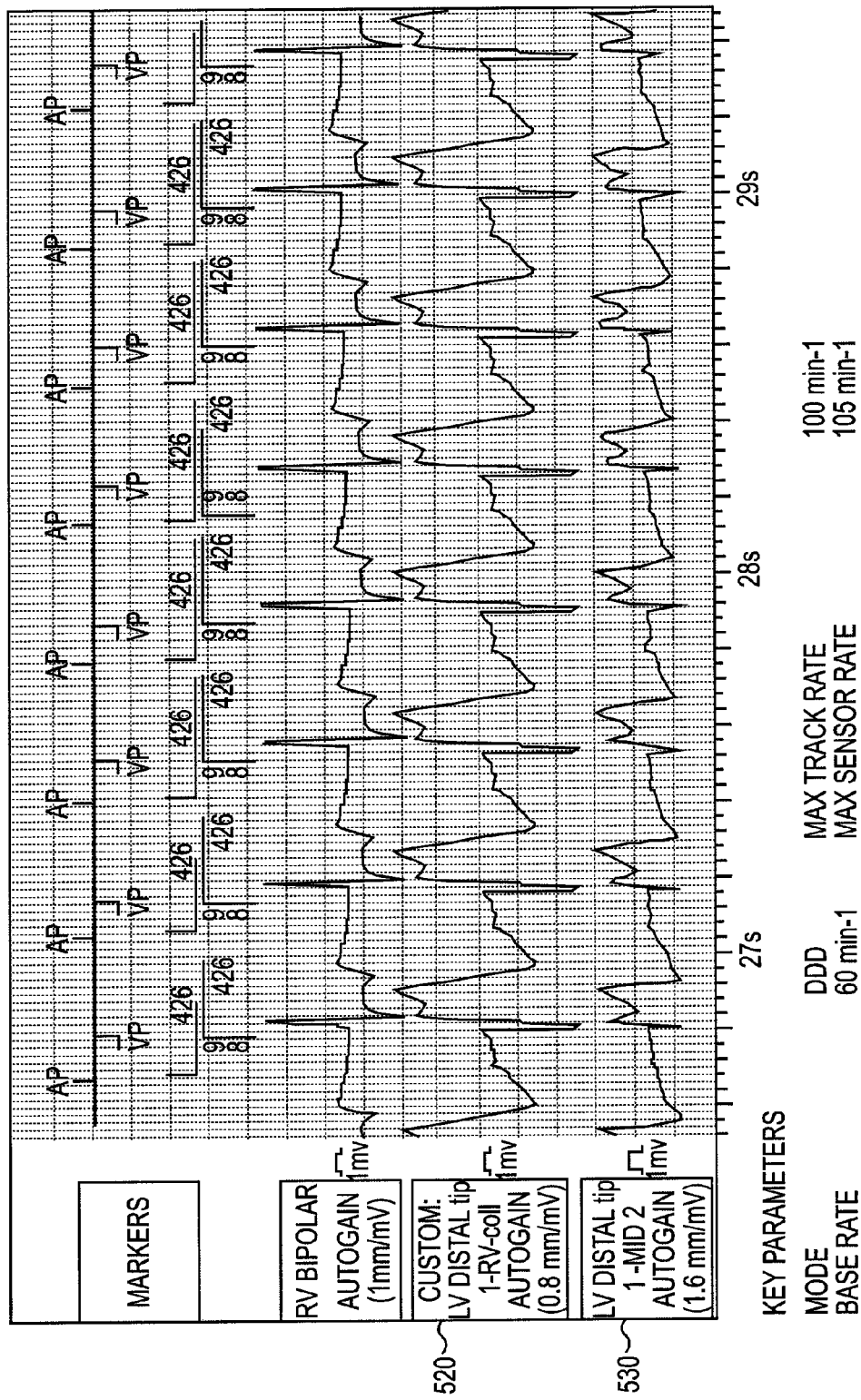

FIG. 5 illustrates EGMs 520, 530 sensed following pacing pulses delivered to two sites of the LV lead. In this example, a first pacing pulse is delivered to the LV using the LV tip D1 as the cathode electrode for the pacing pulse and using the case electrode as the pacing anode electrode. A second pacing pulse is delivered simultaneously to the LV using the first LV ring electrode M2 as the pacing cathode electrode and using the case electrode as the pacing anode electrode. Both pacing pulses produce capture at their respective pacing cathode sites The cardiac electrical activity in the LV is sensed using the same two sensing vectors as in the example of FIG. 4. FIG. 5 shows the EGM trace 520 of the LV distal tip D1 to RV coil sensing vector and the EGM trace 530 of the LV distal tip D1 to LV ring M2 sensing vector. In contrast to the example shown in FIG. 4, when the two pacing pulses produce multi-site capture, the cardiac electrical activity signal shown on the EGM sensed between the LV distal tip D1 to RV coil has a different amplitude when compared the EGM signal sensed between the LV distal tip D1 to the ring electrode M2. The reason for the difference in amplitude arises from the relationship between the vectors used for pacing and those used for sensing. The bipolar EGM has a smaller amplitude when compared to the unipolar EGM because capture is occurring at both sensing electrodes.

In this example, multi-site pacing involves two sites—a first pacing cathode D1 is used to deliver the first pacing pulse and a second pacing cathode M2 is used to deliver the second pacing pulse and both pacing pulses produce capture. The EGM trace 520 that plots the cardiac electrical activity sensed from the D1 to RV coil sensing vector has similar (about equal) amplitude to the single capture scenario of FIG. 4. The similar amplitude occurs because the cardiac electrical activity sensed by the D1 to RV coil sensing vector is dominated by the cardiac electrical activity at D1, which is the captured response present at D1.

The D1 to M2 sensing vector (EGM trace 530) senses cardiac electrical activity at D1 (which is the pacing cathode for the first pacing pulse) and cardiac electrical activity at M2 (which is the pacing cathode for the second pacing pulse). The D1 to M2 sensing vector can be used to generate differential signal between the cardiac activity signal sensed at D1 and the cardiac electrical activity sensed at M2. When capture occurs at both pacing cathode sites, the cardiac electrical activity at D1 and M2 are similar, and they significantly cancel one another in the differential signal, resulting in a smaller amplitude when compared to a signal that is dominated by the captured response at one of the cathode electrodes, in this case, D1.

Figure 6:
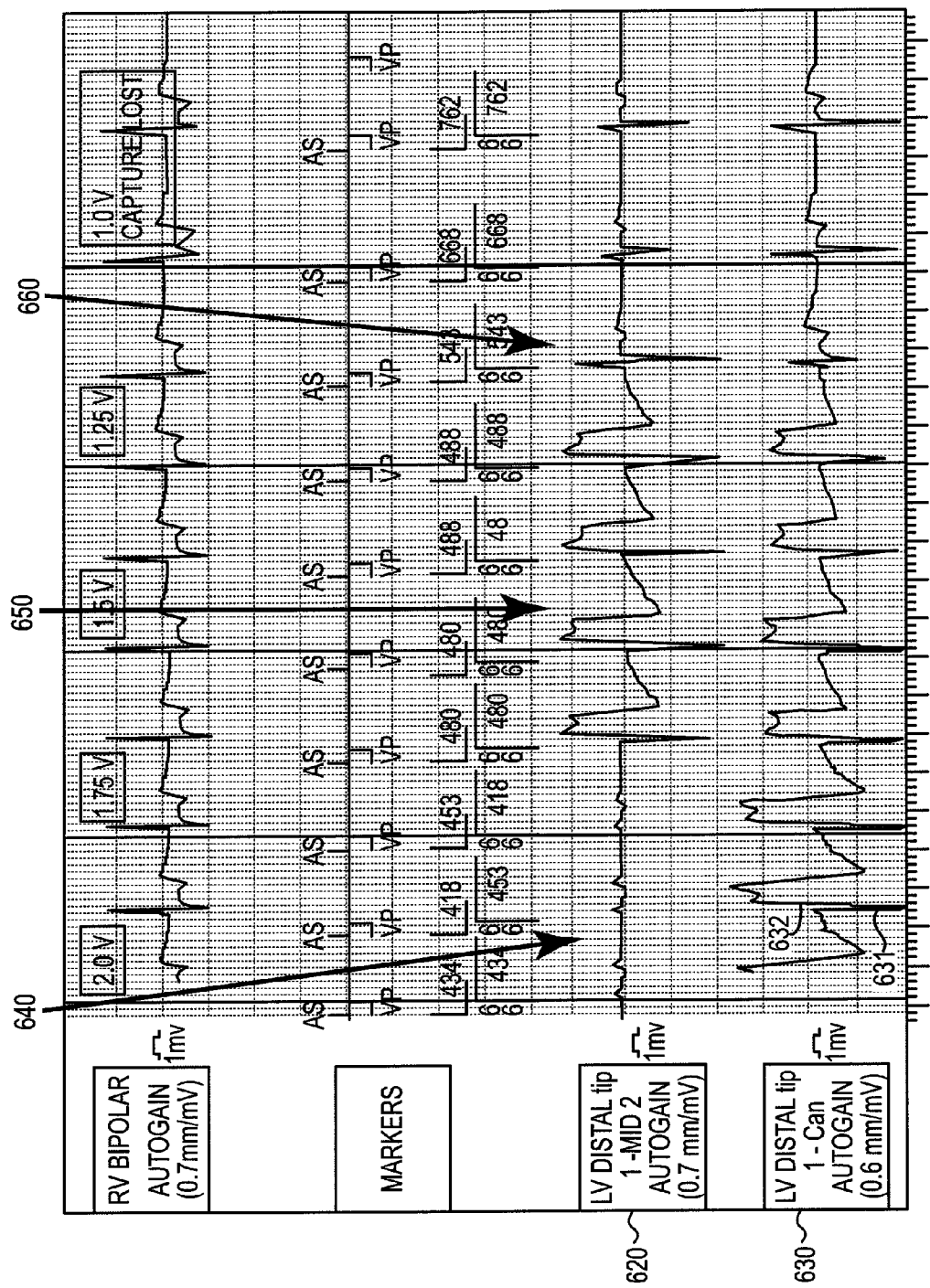

FIG. 6 provides another example of cancellation of sensed cardiac activity when pacing cathodes are used to provide the sensing vector for multi-site pacing in a heart chamber. In this example, a first pacing pulse is delivered to a first site using D1 as the first cathode and the case electrode as the anode, a second pacing pulse is delivered to a second site using M2 as the second cathode and the case electrode as the anode. The first and second pacing pulses are delivered simultaneously during a cardiac cycle.

A first EGM 620 shows the cardiac electrical activity sensed from the first pacing cathode D1 to the second pacing cathode M2. In other words, the first EGM signal 620 is sensed using a bipolar sensing configuration between the two pacing cathodes of the multi-side pacing. A second EGM 630 shows the cardiac electrical activity sensed from the first pacing cathode D1 to the can electrode. In other words, the second EGM signal 630 is sensed using a unipolar sensing configuration between D1 and the can.

The second EGM signal 630 is dominated by the cardiac electrical activity at D1, whereas the first EGM signal 620 is a differential signal that results from cancellation between the cardiac electrical activity at D1 and the cardiac electrical activity at M2. Thus, when capture occurs at both pacing cathodes D1 and M2, as illustrated by the first portion of the EGMs 620, 630, indicated by arrow 640, the unipolar signal sensed between D1 and the can exhibits the characteristic capture morphology having an abrupt negative transition 631 followed by a positive transition 632. However, the first EGM signal 620 is a differential signal in which the captured cardiac activity sensed at D1 and the captured cardiac activity sensed at M2 cancel. Because the cardiac electrical activity at sites D1 and M2 are captured responses, the cancellation results in a smaller signal amplitude having a different morphology, when compared to the amplitude and morphology of EGM 630.

At the second portion of the EGMs 620, 630, indicated by the arrow 650, the pacing pulses delivered to D1 are captured, but the pacing pulses delivered to M2 are not captured. In the second portion indicated by arrow 650, the amplitude and morphology of the first EGM 620 and the second EGM 630 are similar. The similarity arises because the pacing pulses delivered to M2 are not captured, thus cardiac electrical activity sensed at D1 is not substantially cancelled by the cardiac electrical activity at M2. The result is that the first EGM signal 620 is dominated by the capture response at D1, as is the EGM signal 630. The third portion of the EGM signals 620, 630 indicated by arrow 660 illustrates the EGM morphology that results when neither pacing pulse is captured at its respective pacing site.

From observation of the EGM traces 620, 630 shown in FIG. 6, it is apparent that the morphology and amplitude of the differential signal 620 that is that result when pacing pulses at both pacing cathodes produce capture can be distinguished from the amplitude and morphology of the differential signal produced when capture occurs at only one of the pacing cathodes.

For example, in the scenario of FIG. 6, comparing the differential signal generated using the D1 to M2 pacing cathodes in a bipolar sensing vector to an amplitude threshold and/or a known morphology template that characterizes multi-site capture can be used to distinguish between multi-site capture, single site capture, and non capture.

Additionally or alternatively, one or more signals sensed using sensing vectors that produce signals dominated by cardiac electrical activity at one site of the multi-site pacing, e.g., unipolar or extended bipolar sensing vectors, may be used to distinguish between single site capture and multi-site capture or to confirm an initially determined capture status. For example, in one possible embodiment, the capture circuitry is configured to initially determine capture status by distinguishing between single site capture and multi-site capture using the differential signal generated via a bipolar sensing vector that includes the pacing cathodes. The capture status initially identified using the bipolar signal can be confirmed by comparing the bipolar signal to a unipolar signal generated using one of the pace cathodes in the sensing vector.

In another possible scenario, both the bipolar signal and the unipolar signal are used to distinguish multi-site from single site capture. In this scenario, one or more characteristics of the bipolar signal, e.g., amplitude, morphology or both, can compared to corresponding characteristics of the unipolar signal. In some implementations, an amplitude of the bipolar signal is compared to an amplitude of the unipolar signal. Amplitudes that are inconsistent indicate multi-site capture. In some implementations a ratio of amplitudes between the bipolar and unipolar signals is determined and compared to an amplitude ratio threshold. Amplitude ratios that are low, e.g., less than the amplitude ratio threshold indicate multi-site capture. For example, with reference to FIG. 6, the amplitude ratio may be calculated as $A_b/A_u$, where $A_b$ is the amplitude of the bipolar LV distal tip to M2 signal and $A_u$ is the amplitude of the unipolar LV distal tip to can signal.

In yet another implementation, the morphologies of the bipolar and unipolar signals are compared by calculating a correlation coefficient representative of an amount of correlation between the two signals. Morphologies that are inconsistent (low correlation coefficient), indicate multi-site capture.

Note that in some cases, the pacing cathode electrodes are used to provide the sensing vector for the differential signal that is used to distinguish multi-site capture from single site capture. It is also possible, instead of using the pacing cathode electrodes, to use electrodes that are near the pacing cathodes to form the sensing vector. These nearby electrodes are surrogates for the pacing cathodes. For example, in one scenario, the sensing vector for the differential signal includes the first pacing cathode electrode and an electrode that is nearby the second pacing cathode electrode. Although use of nearby surrogate electrodes instead of the pacing cathodes themselves may provide suboptimal cancellation of the cardiac activity in the differential signal, the amount of cancellation may be sufficient to distinguish between multi-site and single site capture and/or in the case of single site capture to determine which pacing pulse was captured and/or to determine if none of the pacing pulses were captured. A similar approach may be used for the additional signal, wherein instead of using a pacing cathode to form the unipolar or extended bipolar sensing vector, a surrogate electrode near the pacing cathode is used.

Figure 7:
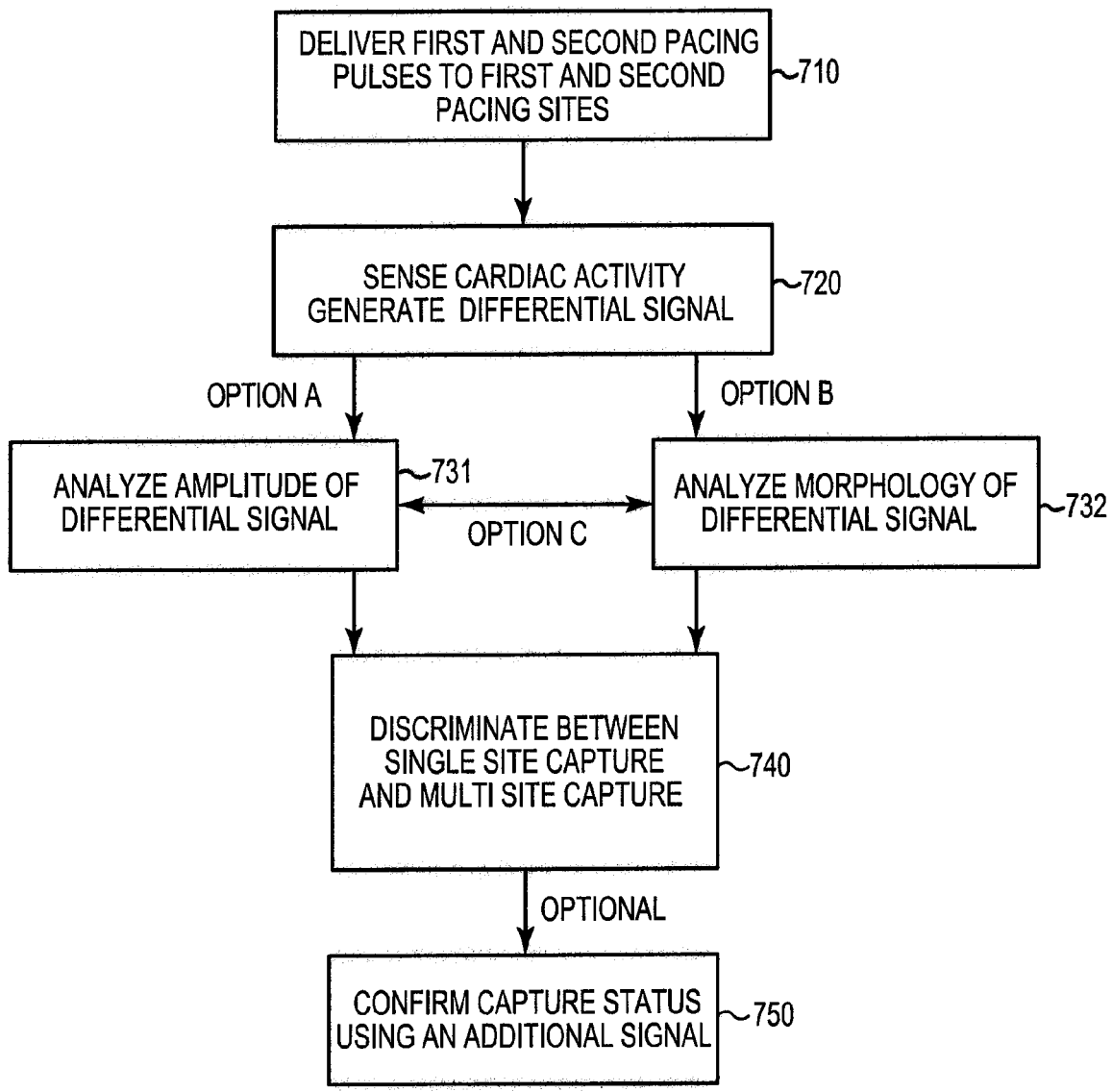
FIG. 7 is a flow diagram of a process for discriminating between multi-site and single site capture based on a differential signal between sensed cardiac electrical activity at first site and sensed cardiac electrical activity at a second cardiac site, the first and second sites being within a single cardiac chamber.

FIG. 7 is a flow diagram that illustrates a process of distinguishing between multi-site capture and single site capture for first and second pacing pulses delivered 710 to first and second pacing sites, respectively, during a cardiac cycle. The pacing pulses are delivered simultaneously or closely spaced in time during a cardiac cycle. Note that the processes outlined in the flow diagrams of FIGS. 7 through 10 for two pacing sites are extendible to more than two pacing sites and is applicable to any heart chamber.

The IMD senses cardiac electrical activity and generates 710 a differential signal, the differential signal involves cancellation of the cardiac electrical activity sensed at one sensing electrode from the cardiac electrical activity sensed at another sensing electrode. Thus, when the cardiac electrical activity sensed at one of the sensing electrodes is similar to the cardiac electrical activity sensed at the other sensing electrode, the differential signal has a relatively small amplitude and a morphology that is distinguishable from a differential signal that is generated when the cardiac electrical activity sensed at one of the sensing electrodes is different from the cardiac electrical activity sensed at the other sensing electrode.

According to OPTION A in FIG. 7, the amplitude of the differential signal may be analyzed 731 by comparing the amplitude of the differential signal to a predetermined amplitude threshold value. If the amplitude of the differential signal is less than the amplitude threshold value, multi-site capture is indicated 740. However, if the amplitude of the differential signal is greater than the amplitude threshold value, single site capture is indicated 740.

According to OPTION B in FIG. 7, the morphology of the differential signal may be analyzed 732 by comparing the morphology of the differential signal to a known morphology. For example, the known morphology may correspond to single site capture. In this case, if the amplitude of the differential signal is inconsistent with the known single site capture morphology, multi-site capture is indicated 740. However, if the morphology of the differential signal is consistent with the known single site capture morphology, single site capture is indicated 740. Comparison of the differential signal morphology to the known morphology may be achieved by calculating a correlation coefficient, for example.

According to OPTION C in FIG. 7, both the amplitude and the morphology of the differential signal may be analyzed 731, 732, e.g., according to the processes outlined above. The capture status determined using processes 710-740 may be confirmed 750 using one or more additional signals which are significantly dominated by cardiac electrical activity produced by one of the pacing pulses, e.g., a unipolar signal. For example, the capture circuitry may compare the amplitude or morphology of the differential signal to an additional signal that is dominated by the cardiac response from one of the pacing sites. Additionally, the capture circuitry may compare the amplitude or morphology of the differential signal to a second additional signal, e.g., a unipolar or extended bipolar signal, that is dominated by the cardiac response from another of the pacing sites.

In some implementations involving pacing at a first site using a first cathode electrode and pacing at a second site using a second cathode electrode, the differential signal is generated from a bipolar pacing vector from the first cathode electrode to the second cathode electrode. For the confirmation process, the capture circuitry may compare the differential signal with an additional signal, e.g., a unipolar signal or extended bipolar signal, that uses the first cathode electrode. The capture circuitry may also optionally compare the differential signal to a second additional signal, e.g., unipolar signal or extended bipolar signal, sensed from the second cathode electrode.

Figure 8:
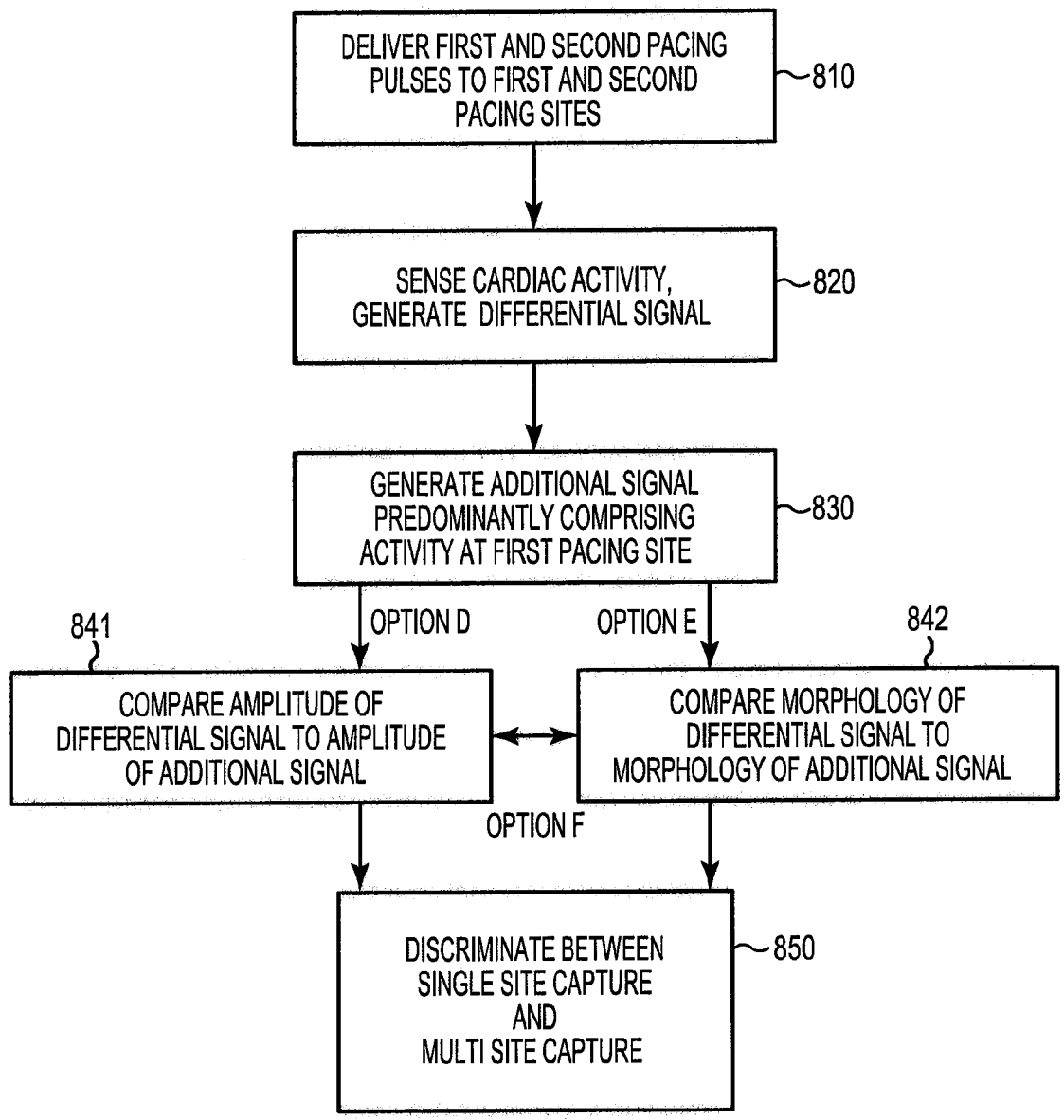
FIG. 8 is a flow diagram of a process for discriminating between multi-site and single site capture based on the differential signal and an additional signal that predominantly includes sensed cardiac electrical activity at one of the first or second sites.

The flow diagram of FIG. 8 illustrates a process wherein both the differential signal and the additional signal are used to distinguish between single site capture and multi-site capture. In this example, a first pacing pulse is delivered 810 to a first pacing site using a first cathode electrode and a second pacing pulse is delivered 810 to the second pacing site using a second cathode electrode. As previously discussed, the pacing pulses are delivered simultaneously or closely spaced in time during a cardiac cycle.

The IMD senses cardiac electrical activity and generates 820 a differential signal as previously described. For example, the differential signal may be generated by bipolar sensing between the two pacing cathodes. The IMD also generates 830 an additional signal, the additional signal predominantly comprising cardiac electrical activity present at one of the pacing sites. In some cases, the electrodes that generate the differential signal are the pacing cathode electrodes which are used in a bipolar sensing arrangement. In some cases, the sensing vector used to generate the additional signal employs one of the pacing cathode electrodes arranged in a unipolar or extended bipolar sensing arrangement.

According to OPTION D shown in FIG. 8, the amplitude of the differential signal is compared 831 to the amplitude of the additional signal. The comparison may involve calculating an amplitude ratio between an amplitude of the differential signal to the amplitude of the additional signal. If the amplitude ratio is less than a programmable amplitude ratio threshold, e.g., about 0.7 or other programmable value, the amplitude of the differential signal is significantly less than the amplitude of the additional signal indicating 850 multi-site capture. However, if the amplitude ratio is greater than the programmable amplitude ratio threshold, single site capture is indicated 850.

According to OPTION E shown in FIG. 8, the morphology of the differential signal is compared 842 to the morphology of the additional signal. The comparison may involve calculating a correlation coefficient between the two signals which indicates a degree of correlation between the morphology of the differential signal and the morphology of the additional signal. If the correlation coefficient is less than a programmable correlation coefficient threshold, e.g., about 0.7, the differential signal and the additional signal are significantly uncorrelated, indicating 850 multi-site capture. However, if the correlation coefficient is greater than the programmable correlation coefficient threshold, single site capture is indicated 850.

According to OPTION F in FIG. 8, both the amplitude and the morphology of the differential signal may be compared 831, 832 to the amplitude and morphology of the additional signal, e.g., according to the processes outlined above, to distinguish multi-site capture from single site capture.

Discrimination between multi-site capture and single site capture and/or determining the capture status of each pacing pulse used in multi-site pacing according to approaches discussed herein may be used for capture threshold testing to determine capture threshold energies of the pacing sites. Alternatively or additionally, discrimination between multi-site capture and single site capture and/or determining the capture status of each pacing pulse used in multi-site pacing according to approaches discussed herein may be used to monitor and/or adjust pacing energy during delivery of a prescribed pacing therapy.

An example of a step down capture threshold test that relies on the approaches discussed above is shown in the flow diagram of FIG. 9. The step down test steps down the pacing energy (amplitude and/or width of the pulse voltage) applied to a test site while the non-test site is held constant until capture is lost at the test site. It will be appreciated that a capture threshold test that steps up the pacing energy of the test site until capture of both the test and non-test sites is achieved may also use the approaches described herein.

Figure 9:
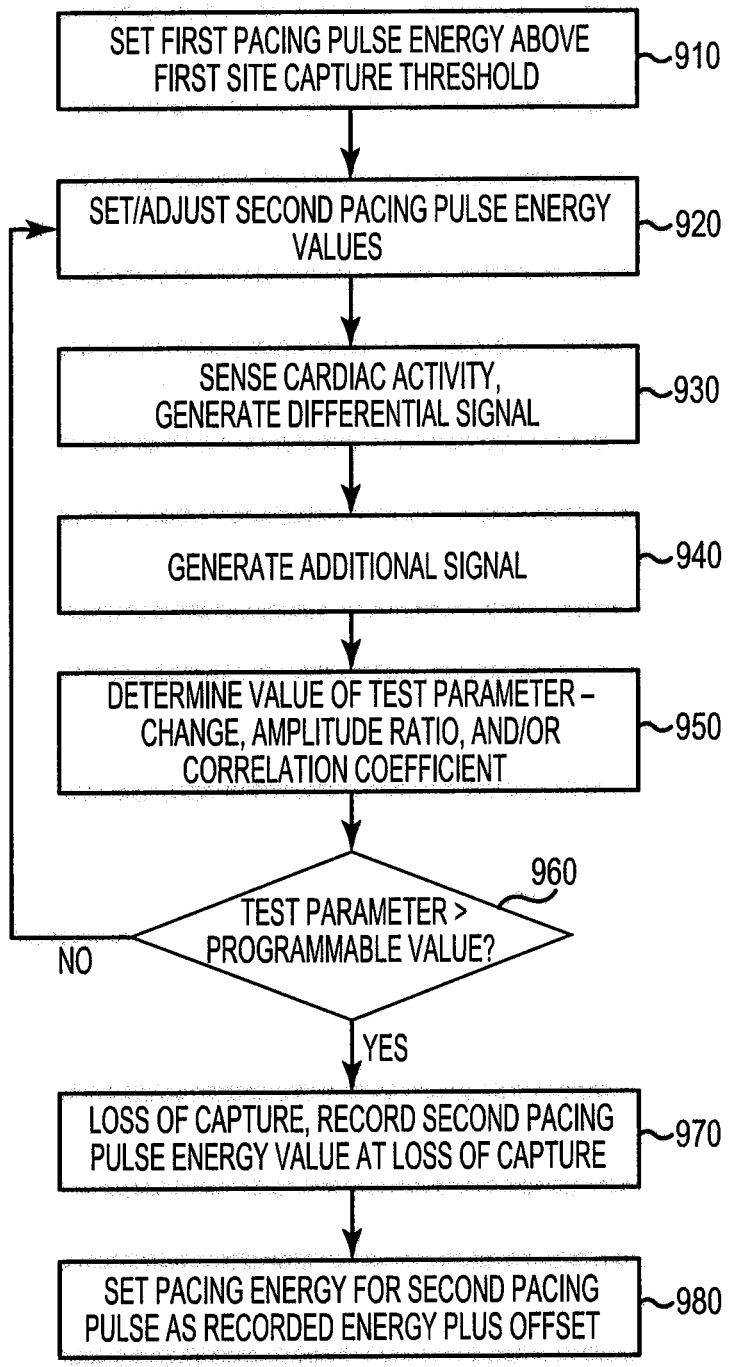
FIG. 9 is a flow diagram illustrating process for determining a capture threshold for multi-site pacing.

As outlined in FIG. 9, during each cardiac cycle of the capture threshold test, a first pacing pulse is delivered to a first site in a cardiac chamber and a second pacing pulse is delivered to a second site in the cardiac chamber. The pacing energy of the first pacing pulses delivered to the first pacing site for the cardiac cycles of the capture threshold test is set 910 to a value that is known to be above the capture threshold for the first site. The first pacing site is the non-test site in this example. The pacing energy for the second pacing pulse is initially set to a high value that is expected to result in capture at the second pacing site, which is the test site for this example. The energy of the second pacing pulse is iteratively decreased 920 over a number of cardiac cycles of the capture threshold test while the energy of the first pacing pulse is held constant.

A first pacing pulse is delivered to the first pacing site using a first cathode electrode and a second pacing pulse is delivered to the second site using a second cathode electrode during each cardiac cycle. Following delivery of the first and second pacing pulses for a cardiac cycle, a differential signal is generated 930 between sensed cardiac electrical activity at the first pacing site and sensed cardiac electrical activity at the second pacing site. An additional signal is generated 940 that predominantly includes cardiac activity sensed at the first pacing site. In some implementations, the differential signal is generated from a bipolar sensing vector that uses the first pacing cathode electrode and the second pacing cathode electrode and the additional signal is generated from a unipolar or extended bipolar sensing vector that uses the first pacing cathode electrode and the case electrode, the RV coil electrode, or the SVC coil electrode.

A value of a test parameter for the cardiac cycle is calculated 950 based on the differential and additional signals. For example, in some scenarios, calculating the value of the test parameter comprises calculating a ratio between the amplitude of the differential signal and the amplitude of the additional signal. If the amplitude ratio is below 960 an amplitude ratio threshold value, e.g., 0.5, then this indicates capture at both the test site and the non-test site. However If the value of the amplitude ratio is above 960 the amplitude ratio threshold value, this indicates that the second pacing pulse did not capture at the test site.

Note that in some scenarios, calculating the value of the test parameter may comprise calculating a correlation coefficient that compares the morphology of the differential signal to the additional signal as an alternative to or in addition to the amplitude ratio. If the correlation coefficient is below 960 a correlation coefficient threshold value, e.g., 0.7, then capture at both the test site and the non-test site is indicated. However If the value of the correlation coefficient is above 960 the correlation coefficient threshold value, then loss of capture by the second pacing pulse at the test site is indicated. Note that other types of test parameters may be used to compare the differential signal to the additional signal are contemplated in conjunction with the embodiments described herein.

If the change in status from multi-site capture to single site capture is indicated by the comparisons, the capture threshold is recorded 970 as the last pacing energy that produced capture. A suitable energy for pacing can be set 980 as the capture threshold for the second site plus an appropriate safety factor, e.g., 0.25 V.

The approaches discussed herein can be used for capture verification in conjunction with a therapeutic multi-site pacing protocol. Capture verification differs from a capture threshold testing in that there is no test site for which the pacing energy stepped down (or stepped up) to determine the capture threshold. In the context of the embodiments discussed herein, capture verification involves determining the capture status of multi-site paces for one or more cardiac cycles delivered during a multi-site pacing therapy. Such capture verification processes can be referred to as "beat-to-beat" capture verification, although these processes do not necessarily require that testing for capture occurs for every cardiac cycle or that the cardiac cycles for which capture verification is performed are temporally contiguous. For example, in some scenarios, a sample of cardiac cycles, e.g., a random sample or other type sample, can be verified for multi-site capture.

Figure 10:
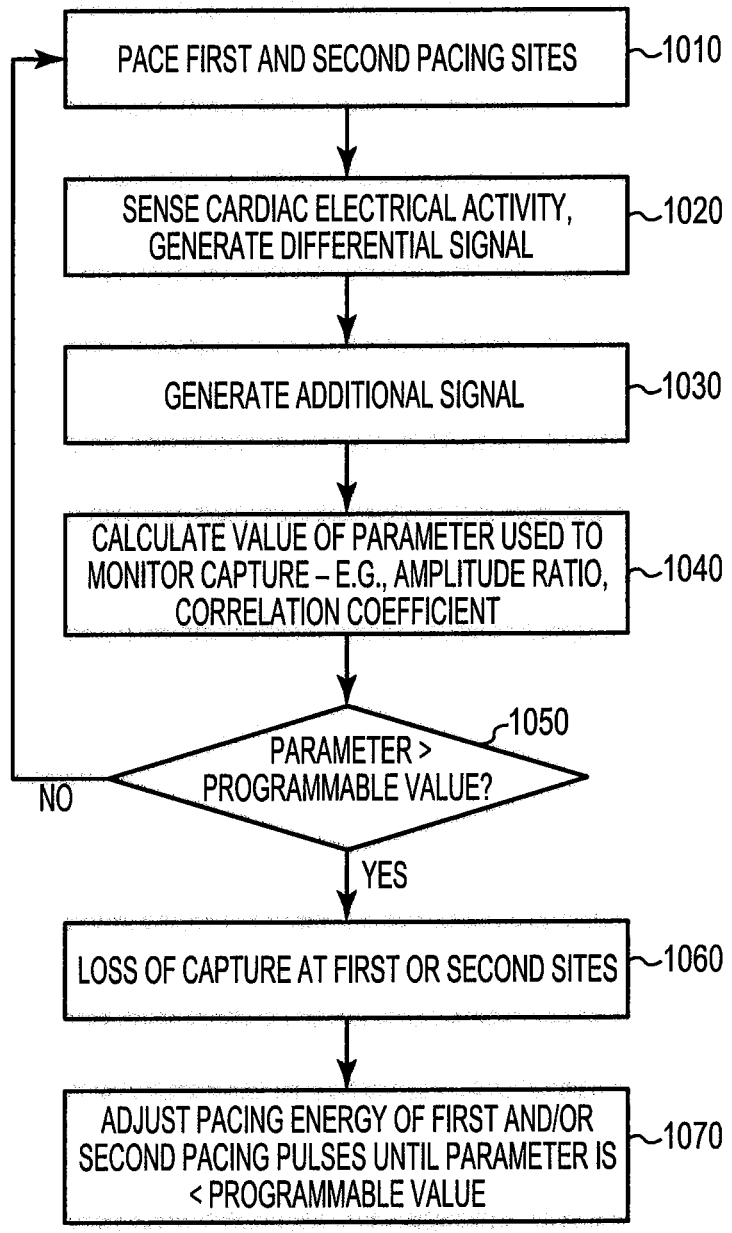
FIG. 10 is a flow diagram illustrating a process for performing capture verification for multi-site pacing.

An example of capture verification for multi-site pacing is illustrated in the flow diagram of FIG. 10. In this example, the multi-site pacing involves pacing at two pacing sites in a cardiac chamber. It will be appreciated that the approaches described herein are also applicable to multi-site pacing that involves pacing at more than two sites in a cardiac chamber.

First and second pacing pulses are delivered 1010 to first and second sites of a cardiac chamber during a cardiac cycle using first and second pacing cathode electrodes, respectively. Following delivery of the first and second pacing pulses, a differential signal is generated 1020 between cardiac electrical activity sensed at the first pacing site, e.g., via the first pacing cathode and cardiac electrical activity sensed at the second pacing site, e.g., through the second pacing cathode. An additional signal is generated 1030 that is based predominantly on cardiac activity sensed at the first pacing site, e.g., through the first pacing cathode. In some implementations, the differential signal is generated from a bipolar sensing vector that uses the first pacing cathode electrode and the second pacing cathode electrode, and the additional signal is generated from a unipolar or extended bipolar sensing vector that uses the first pacing cathode electrode and the case electrode, the RV coil electrode, or the SVC coil electrode.

A value of a parameter used for monitoring the capture status of the multi-site pacing is calculated 1040 based on the differential and additional signal. For example, in some scenarios, calculating the value of the parameter comprises calculating a ratio between the amplitude of the differential signal and the amplitude of the additional signal. If the amplitude ratio is below 1050 an amplitude ratio threshold value, e.g., 0.7, then this indicates capture by both the first and second pacing pulses. However If the value of the amplitude ratio is above 1050 the amplitude ratio threshold value, this indicates that the second pacing pulse did not capture at the test site.

Note that in some scenarios, calculating the value of the test parameter may comprise calculating a correlation coefficient that compares the morphology of the differential signal to the additional signal as an alternative to or in addition to the amplitude ratio. If the correlation coefficient is below 1050 a correlation coefficient threshold value, e.g., 0.7, then capture by both the first pacing pulse and the second pacing pulse is indicated. However If the value of the correlation coefficient is above 1050 the correlation coefficient threshold value, then loss of capture by one of the first or the second pacing pulse is indicated. Note that other types of parameters to monitor the capture status may be used, e.g., peak widths, peak timing, etc., to compare the differential signal to the additional signal are contemplated and may be used in conjunction with the embodiments described herein.

If the change in status from multi-site capture to single site capture is indicated 1060 by the comparisons, then the pacing energy of the first and/or second pacing pulses may be adjusted until the value of the monitoring parameter is above the programmable value. Alternatively or additionally, if a change in status from multi-site capture to single site capture is indicated 1060, then a capture threshold test may be performed or scheduled by the IMD to reassess the capture thresholds at one or both of the first and second pacing site.

Note that if the cardiac activity at the first pacing site dominates the additional signal and the first pacing pulse loses capture at the first pacing site, then there will be low correlation between the differential signal and the additional signal. Thus, when the correlation coefficient between the differential and additional signal is low (or the amplitude ratio low), then, in addition to the possibility of multi-site capture, there is also a possibility that the first pacing pulse is no longer capturing. In this scenario, the capture circuitry may compare the amplitude of the additional signal to an amplitude threshold to confirm that the first pacing pulse is producing capture. Then, if the amplitude of the additional signal is higher than the amplitude threshold and the correlation (or amplitude ratio) between the additional signal and the differential signal is low, multi-site capture is indicated. If the amplitude of the additional signal is lower than the amplitude threshold and the correlation (or amplitude ratio) between the additional signal and the differential signal is high, then single site capture with non capture by the second pacing pulse is indicated. If the amplitude of the additional signal is lower than the amplitude threshold and the correlation between the additional signal and the differential signal is low, then single site capture with non capture by the first pacing pulse is indicated. In some implementations, heart rate information may be used to identify loss of capture at both pacing electrodes.

Generation of the differential signal may be implemented in several ways. For example, in one scenario, each pacing cathode electrode (or nearby surrogate) may be coupled to an input of a differential amplifier. The differential amplifier generates the differential signal at its output. In another scenario, each pacing cathode (or nearby surrogate) may be used in a unipolar or extended bipolar sensing vector to sense cardiac activity produced by the cardiac response at the pacing cathode. The two signals produced from this sensing may be subtracted from each other, e.g., in the signal processing circuitry, the capture circuitry, the controller or elsewhere. In some cases, the two signals may be subtracted after the sensed signals are converted from analog to digital form. The difference signal resulting from the subtraction generates the differential signal having the characteristics previously described.

In the preceding detailed description, reference is made to the accompanying drawings which form a part hereof, and in which are shown by way of illustration specific embodiments in which the subject matter disclosed herein may be practiced. These embodiments, which are also referred to herein as "examples," are described in sufficient detail to enable those skilled in the art to practice the subject matter disclosed herein.

In the above description, like numerals or reference designators are used to refer to like parts or elements throughout. The terms "a" or "an" are used, as is common in patent documents, to include one or more than one. In this document, the term "or" is used to refer to a nonexclusive or, unless otherwise indicated.

In the above description and the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. The scope of the invention should, therefore, be determined with reference to the appended claims, along with the full scope of equivalents to which such claims are entitled.

What is claimed is:

1. A medical device, comprising:
   implantable electrodes including at least a first electrode configured to be disposed at a first site of a heart chamber and a second electrode configured to be disposed at a second site of the heart chamber;
   pacing circuitry configured to deliver a first pacing pulse to the first site using the first electrode as a cathode electrode for the first pacing pulse and to deliver a second pacing pulse to the second site using the second electrode as a cathode electrode for the second pacing pulse, the first pacing pulse and the second pacing pulse delivered during a cardiac cycle;
   sensing circuitry configured to sense a cardiac response to the pacing pulses including sensing cardiac electrical activity using the implantable electrodes, the sensing circuitry further configured to generate a differential signal between sensed cardiac electrical activity at the first electrode and sensed cardiac electrical activity at the second electrode; and
   capture circuitry configured to discriminate between single site capture, comprising capture by one of the first pacing pulse or the second pacing pulse, and multi-site capture, comprising capture by both the first pacing pulse and the second pacing pulse, based on the differential signal.

2. The medical device of claim 1, wherein the capture circuitry is configured to discriminate between single site capture and multi-site capture based on one or both of amplitude and morphology of the differential signal.

3. The medical device of claim 1, wherein the capture circuitry is configured to:
   discriminate between single site capture and multi-site capture based on one or both of amplitude and morphology of the differential signal; and
   confirm single site capture or confirm multi-site capture by comparison of the differential signal to at least one additional signal, the at least one additional signal predominantly comprising a captured response signal produced by the first pacing pulse and sensed at the first pacing site.

4. The medical device of claim 1, wherein:
   the sensing circuitry is configured to generate at least one additional signal, the additional signal predominantly comprising a captured response signal produced by the first pacing pulse and sensed between the first electrode and a third electrode; and
   the capture circuitry is configured to compare the differential signal to the additional signal and to discriminate between single site capture and multi-site capture based on comparison between the differential signal and the additional signal.

5. The medical device of claim 4, wherein the third electrode comprises an electrode disposed on an implantable housing of the medical device.

6. The medical device of claim 5, wherein the third electrode is disposed in or on another heart chamber.

7. The medical device of claim 4, wherein the capture circuitry is configured to detect multi-site capture if an amplitude of the differential signal is a predetermined amount less than an amplitude of the additional signal or if a ratio between an amplitude of the differential signal and an amplitude of the additional signal is below an amplitude ratio threshold value.

8. The medical device of claim 4, wherein the capture circuitry is configured to detect multi-site capture if morphology of the differential signal is inconsistent with morphology of the additional signal.

9. The medical device of claim 1, wherein the capture circuitry is disposed within an implantable housing.

10. The medical device of claim 1, wherein the capture circuitry is disposed within a patent external device.

11. The medical device of claim 1, wherein the capture circuitry is configured to perform a capture threshold test to determine a capture threshold of the second site, the capture threshold test configured to:
    deliver first and second pacing pulses to the first and second sites, respectively during multiple cycles of the capture threshold test,
    maintain a pacing energy of the first pacing pulses above a capture threshold for the first site, and
    step down or step up a pacing energy of the second pacing pulses until a change in capture status is detected,
    wherein the change in capture status occurs if
    multi-site capture is detected for a first cardiac cycle and single site capture is detected for one or more cardiac cycles following the first cardiac cycle when the energy of the second pacing pulses is stepped down during the capture threshold test, or
    single site capture is detected for a first cardiac cycle and multi-site capture is detected for one or more cardiac cycles following the first cardiac cycle if the energy of the second pacing pulses is stepped up during the capture threshold test.

12. A medical device, comprising:
    a plurality of electrodes configured to be respectively coupled to a heart chamber at a plurality of sites;

a pulse generator configured to deliver during a cardiac cycle:
   a first pacing pulse using a first pacing cathode electrode of the plurality of electrodes, and
   a second pacing pulse using a second pacing cathode electrode of the plurality of electrodes;
sensing circuitry comprising a first sensing electrode and a second sensing electrode, the sensing circuitry configured to sense a cardiac response to the pacing pulses, including sensing cardiac electrical activity at the first sensing electrode and at the second sensing electrode, the sensing circuitry further configured to develop a differential signal between cardiac electrical activity sensed at the first sensing electrode from cardiac electrical activity sensed at the second sensing electrode; and
capture circuitry configured to discriminate between single site capture by one of the first or second pacing pulses and multi-site capture by both the first and second pacing pulses based on the differential signal.

13. The device of claim 12, wherein the first sensing electrode is the first pacing cathode electrode and the second sensing electrode is the second pacing cathode electrode.

14. The device of claim 12, wherein the plurality of electrodes are disposed on a multi-electrode lead and the first sensing electrode comprises an electrode adjacent to the first pacing cathode electrode on the multi-electrode lead.

15. The medical device of claim 12, wherein the sensing circuitry comprises a differential amplifier having first and second differential inputs and the first sensing electrode is electrically coupled to the first differential input and the second sensing electrode is electrically coupled to the second differential input.

16. The medical device of claim 12, wherein the sensing circuitry comprises circuitry configured to develop the differential signal by subtracting a first signal comprising cardiac electrical activity sensed using the first sensing electrode from a second signal comprising cardiac electrical activity sensed using the second sensing electrode.

17. A method, comprising:
delivering a first pacing pulse to a first site of a cardiac chamber using a first electrode as a cathode electrode for the first pacing pulse;
delivering a second pacing pulse to a second site of the cardiac chamber using a second electrode as a cathode electrode for the second pacing pulse, the first and second pacing pulses delivered during a cardiac cycle;
sensing cardiac activity at the first and second electrodes;
generating a differential signal between the cardiac activity sensed at the first electrode and the cardiac activity sensed at the second electrode following delivery of the first and second pacing pulses;
determining capture status of the first and second pacing pulses including discriminating between single site capture by one of the first or second pacing pulses and multi-site capture by both the first and second pacing pulses based on the differential signal; and
modifying one or both of an energy of a subsequent first pacing pulse and an energy of a subsequent second pacing pulse based on the capture status.

18. The method of claim 17, further comprising generating at least one additional signal comprising cardiac activity sensed between one of the first or second electrodes and a third electrode, wherein discriminating between single capture and multi-site capture comprises comparing the differential signal to the additional signal.

19. The method of claim 17, wherein determining the capture status of the first and second pacing pulses comprises determining one or more of non capture by the first pacing pulse and non capture by the second pacing pulse.

20. The method of claim 17, wherein delivering the first pacing pulse and delivering the second pacing pulse comprises timing an intersite pacing delay between delivering the first pacing pulse and delivering the second pacing pulse.

* * * * *